US011758948B2

(12) United States Patent
Ricketts et al.

(10) Patent No.: US 11,758,948 B2
(45) Date of Patent: Sep. 19, 2023

(54) LIGHTING UNIT FOR AEROSOL-GENERATING SYSTEMS

(71) Applicant: Altria Client Services LLC, Richmond, VA (US)

(72) Inventors: Nikolaus Martin Ernest Wilhelm Ricketts, Geneva (CH); Philippe Slama, Pully (CH)

(73) Assignee: Altria Client Services LLC, Richmond, VA (US)

( * ) Notice: Subject to any disclaimer, the term of this patent is extended or adjusted under 35 U.S.C. 154(b) by 800 days.

(21) Appl. No.: 16/260,695

(22) Filed: Jan. 29, 2019

(65) Prior Publication Data

US 2019/0231997 A1 Aug. 1, 2019

Related U.S. Application Data

(63) Continuation of application No. PCT/EP2018/086347, filed on Dec. 20, 2018.

(30) Foreign Application Priority Data

Jan. 29, 2018 (EP) .................................... 18153886

(51) Int. Cl.
*A24F 40/10* (2020.01)
*A24F 40/60* (2020.01)
(Continued)

(52) U.S. Cl.
CPC .............. *A24F 40/60* (2020.01); *A24F 40/42* (2020.01); *A61M 15/06* (2013.01); *A24F 40/10* (2020.01); *A61M 2205/587* (2013.01)

(58) Field of Classification Search
CPC ...... A24F 47/00; A24F 47/002; A24F 47/008; A24F 40/60; A24F 40/10; A24F 40/40
See application file for complete search history.

(56) References Cited

U.S. PATENT DOCUMENTS 9,427,711 B2 8/2016 Terry et al.
2007/0194712 A1 8/2007 Shiraishi et al.
(Continued)

FOREIGN PATENT DOCUMENTS

CN 203986094 U 12/2014
CN 204540813 U 8/2015
(Continued)

OTHER PUBLICATIONS

International Search Report and Written Opinion for corresponding Application No. PCT/EP2018/086347 dated Mar. 25. 2019.
(Continued)

*Primary Examiner* — Alex B Efta
(74) *Attorney, Agent, or Firm* — Harness, Dickey & Pierce, P.L.C.

(57) ABSTRACT

A cartridge for use with an aerosol-generating system has a housing defining a liquid containing volume. The housing includes a sidewall extending from a mouthpiece end to a power supply end. The housing includes a transparent region forming at least a portion of the sidewall. The housing includes a light source fixed to the sidewall. The light source is configured to transmit light into the liquid containing volume. The light source may be fixed to an inner surface of the sidewall, fixed to an outer surface of the sidewall, or form a portion or the sidewall.

14 Claims, 4 Drawing Sheets

(51) Int. Cl.
*A24F 40/42* (2020.01)
*A61M 15/06* (2006.01)

(56) References Cited

U.S. PATENT DOCUMENTS

| | | | |
|---|---|---|---|
| 2012/0105424 A1 | 5/2012 | Lee et al. | |
| 2013/0192623 A1* | 8/2013 | Tucker | H05B 3/12 131/329 |
| 2014/0366897 A1* | 12/2014 | Liu | A24F 40/60 131/329 |
| 2015/0181930 A1 | 7/2015 | Liu | |
| 2015/0189695 A1* | 7/2015 | Xiang | A24F 40/60 219/209 |
| 2015/0216233 A1* | 8/2015 | Sears | F21V 33/004 362/230 |
| 2015/0328415 A1* | 11/2015 | Minskoff | A61M 15/0043 128/202.21 |
| 2016/0262453 A1* | 9/2016 | Ampolini | A24F 40/40 |
| 2017/0181471 A1 | 6/2017 | Phillips et al. | |
| 2017/0340009 A1 | 11/2017 | Hon | |
| 2018/0098574 A1* | 4/2018 | Sur | G01F 23/292 |
| 2018/0360119 A1* | 12/2018 | Kuwa | A24F 7/00 |

FOREIGN PATENT DOCUMENTS

| | | | | |
|---|---|---|---|---|
| CN | 105125222 A | | 12/2015 | |
| GB | 191507513 A | * | 3/1919 | G01L 7/18 |
| JP | 2007-208041 A | | 8/2007 | |
| JP | 2014-503835 A | | 2/2014 | |
| JP | 2015-505474 A | | 2/2015 | |
| RU | 2608915 C2 | | 1/2017 | |
| WO | WO-2015120356 A1 | | 8/2015 | |
| WO | WO-2015131428 A1 | | 9/2015 | |
| WO | WO-2015149403 A1 | | 10/2015 | |
| WO | WO-2016101202 A1 | | 6/2016 | |
| WO | WO-2016112542 A1 | | 7/2016 | |
| WO | WO-2016/144966 A1 | | 9/2016 | |
| WO | WO-2017/155277 A1 | | 9/2017 | |

OTHER PUBLICATIONS

International Preliminary Report on Patentability for corresponding Application No. PCT/EP2018/086347, dated Aug. 13, 2020.
Extended European Search Report for Application No. 18153886.9 Published Jul. 20, 2018.
Russian Office Action for corresponding Application No. 2020121189, dated Nov. 23, 2021, English translation included herewith.
European Notice of Allowance for corresponding Application No. 18829382.3, dated Apr. 20, 2022.
Brazilian Office Action for corresponding Application No. 112020012481-4, dated Jul. 21, 2022, with English Translation.
Office Action dated Jan. 23, 2023 issued in related Japanese patent application No. 2020-539251.

* cited by examiner

LIGHTING UNIT FOR AEROSOL-GENERATING SYSTEMS

CROSS-REFERENCE TO RELATED APPLICATIONS

This application is a continuation of, and claims priority to, international application no. PCT/EP2018/086347, filed on Dec. 20, 2018, and further claims priority under 35 U.S.C. § 119 to European Patent Application No. 18153886.9, filed Jan. 29, 2018, the entire contents of each of which are incorporated herein by reference.

BACKGROUND

Field

Example embodiments relate to a lighting unit for aerosol-generating systems, and to a cartridge with a light source that illuminates a portion of the cartridge.

Description of Related Art

Smoking articles, such as an aerosol-generating system, vaporizes a liquid solution (termed as e-liquid). The aerosol-generating system typically includes various components, such as but not limited to, a power supply, an atomizer, a cartridge, and a mouthpiece. The cartridge stores and carries the e-liquid. The atomizer is powered by the power supply and is in fluid communication with the cartridge. Upon actuation of the aerosol-generating system, the atomizer extracts a portion of the e-liquid from the cartridge and aerosolizes it.

The cartridge of the aerosol-generating system is a replaceable liquid container that carries the e-liquid. The cartridge usually includes a transparent housing (or a housing with a transparent window), which allows an adult vaper to view a level and/or quantity of remaining e-liquid in the cartridge of the aerosol-generating system.

In low environment lighting conditions, the aerosol-generating system is not clearly visible. In such situations, an adult vaper may not be able to clearly view and determine the level and/or quantity of the remaining e-liquid in the cartridge of the aerosol-generating system.

SUMMARY

At least one example embodiment relates to a cartridge for an aerosol-generating system.

In at least one example embodiment, a cartridge for use with an aerosol-generating system comprises a housing defining a liquid containing volume. The housing includes a sidewall extending from a mouthpiece end to a power supply end of the housing. The cartridge also comprises a transparent region forming at least a portion of the sidewall and a light source fixed to the sidewall and configured to transmit light into the liquid containing volume.

In at least one example embodiment, the cartridge further comprises an electrical interface electrically connected to the light source and coupled to the sidewall, the housing, or both the sidewall and the housing.

In at least one example embodiment, the light source is fixed to an inner surface of the sidewall.

In at least one example embodiment, the light source is fixed to an outer surface of the sidewall and transmits light through the transparent region.

In at least one example embodiment, the light source forms a portion of the sidewall.

In at least one example embodiment, the light source defines an annular ring portion of the sidewall.

In at least one example embodiment, a portion of an inner surface of the sidewall includes a light reflective layer.

In at least one example embodiment, the transparent region comprises an anti-reflective coating.

In at least one example embodiment, the light source comprises a solid-state light source. In at least one example embodiment, the solid-state light source is a light emitting diodes. In at least one example embodiment, the light source comprises a radioluminescence material. In at least one example embodiment, the radioluminescence material comprises radium, promethium, tritium, a sub-combination thereof, or a combination thereof. In at least one example embodiment, the light source emits light wavelengths in a range from 420 to 720 nm.

At least one example embodiment relates to an aerosol-generating system.

In at least one example embodiment, an aerosol-generating system comprises a power supply, an atomizer electrically coupled to the power supply, and a cartridge. In at least one example embodiment, a cartridge for use with an aerosol-generating system comprises a housing defining a liquid containing volume. The housing includes a sidewall extending from a mouthpiece end to a power supply end of the housing. The cartridge also comprises a transparent region forming at least a portion of the sidewall and a light source fixed to the sidewall and configured to transmit light into the liquid containing volume.

In at least one example embodiment, the power supply comprises a complementary electrical interface electrically coupled to the electrical interface of the light source.

In at least one example embodiment, the aerosol-generating system further comprises a control circuit coupled to the light source configured to illuminate the light source independently from activating the atomizer.

In at least one example embodiment, the aerosol-generating system further comprises a light sensor coupled to the light source.

BRIEF DESCRIPTION OF THE DRAWINGS

Example embodiments will now be described, by way of example only, with reference to the accompanying drawings.

DETAILED DESCRIPTION

Figure 1:
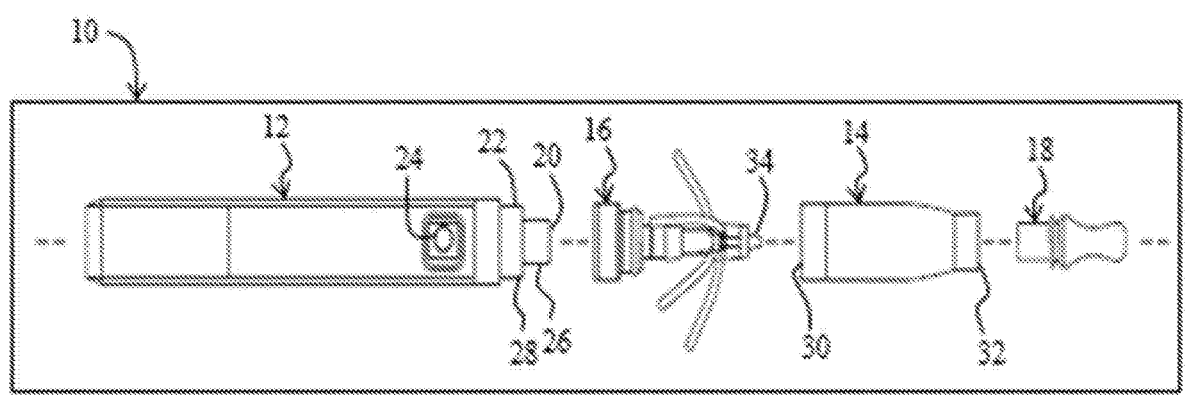
FIG. 1 is an exploded view schematic diagram of an illustrative aerosol-generating system according to at least one example embodiment.

At least one example embodiment relates to a cartridge (or e-liquid reservoir) for use with an aerosol-generating system. The cartridge may have: a housing defining a liquid containing volume, the housing including a sidewall extending from a mouthpiece end to a power supply end; a transparent region forming at least a portion of the sidewall;

and a light source fixed to the sidewall and configured to transmit light into the liquid containing volume.

In at least one example embodiment, the light source may be fixed to an inner surface of the sidewall, or fixed to an outer surface of the sidewall, or form a portion or the sidewall.

In at least one example embodiment, the sidewall inner surface may include a light reflecting layer. The light reflecting layer may efficiently recycle light and direct light toward the light transparent region.

In at least one example embodiment, the light transparent region may include an anti-reflective coating. The anti-reflective coating may provide clear viewing through the light transparent region.

At least one example embodiment relates to an aerosol-generating system. In at least one example embodiment, an aerosol-generating system comprises, a power supply; an atomizer electrically coupled to the power supply; and the cartridge described herein, coupled to the atomizer.

In at least one example embodiment, the power supply may include a complementary electrical interface electrically coupled to the electrical interface of the light source.

In at least one example embodiment, a cartridge includes a housing defining a liquid containing volume. The housing includes a sidewall extending from a mouthpiece end to a power supply end. A transparent region forms at least a portion of the sidewall. A light source is fixed to the sidewall and configured to transmit light into the liquid containing volume.

In at least one example embodiment, an aerosol-generating system includes a power supply, an atomizer electrically coupled to the power supply, and the cartridge according to any preceding claim, coupled to the atomizer.

In at least one example embodiment, the cartridge further includes an electrical interface electrically connected to the light source and coupled to the sidewall or housing.

In at least one example embodiment, the light source is fixed to an inner surface of the sidewall.

In at least one example embodiment, the light source is fixed to an outer surface of the sidewall and transmits light through the sidewall.

In at least one example embodiment, the light source forms a portion of the sidewall. In at least one example embodiment, the light source defines an annular ring portion of the sidewall.

In at least one example embodiment, a portion of the sidewall inner surface includes a light reflective layer.

In at least one example embodiment, the light transparent region comprises an anti-reflective coating.

In at least one example embodiment, the light source comprises a solid-state light source, such as light emitting diodes.

In at least one example embodiment, the light source comprises a radioluminescence material, such as radium, promethium or tritium.

In at least one example embodiment, the light source emits light wavelengths in a range from about 420 to about 720 nanometres (nm).

In at least one example embodiment, the power supply comprises a complementary electrical interface electrically coupled to the electrical interface of the light source.

In at least one example embodiment, the aerosol-generating system includes a control circuit coupled to the light source configured to illuminate the light source independently from activating the atomizer.

In at least one example embodiment, the aerosol-generating system includes a light sensor, the light source operably coupled to the light sensor.

Utilizing the cartridge with a light source fixed to a sidewall of the cartridge may provide a backlit cartridge that may efficiency illuminate the contents of the cartridge. A light reflecting layer on the inner surface of the cartridge may efficiently recycle light and direct light toward the light transparent region, thus reducing lighting power requirements. An anti-reflective coating may provide clear viewing through the light transparent region. These features may enhance the visual effect of the aerosol-generating system.

All scientific and technical terms used herein have meanings commonly used in the art unless otherwise specified. The definitions provided herein are to facilitate understanding of certain terms used frequently herein.

The term "aerosol-generating system" refers to a device configured to use an aerosol-generating substrate to generate aerosol. The aerosol-generating system may also include an aerosolizer, such as an atomizer, cartomizer, or heater. The aerosol-generating system may be an electronic vaping device.

The term "aerosol-generating substrate" refers to a device or substrate that releases, upon heating, volatile compounds that may form an aerosol to be inhaled by a user. Suitable aerosol-generating substrates may include plant-based material. For example, the aerosol-generating substrate may include tobacco or a tobacco-containing material containing volatile tobacco flavor compounds, which are released from the aerosol-generating substrate upon heating. In addition, or alternatively, an aerosol-generating substrate may include a non-tobacco containing material. The aerosol-generating substrate may include homogenized plant-based material. The aerosol-generating substrate may include at least one aerosol former. The aerosol-generating substrate may include other additives and ingredients such as flavorants. The aerosol-generating substrate may be a liquid at room temperature. For example, the aerosol forming substrate may be a liquid solution, suspension, dispersion or the like. In some example embodiments, the aerosol-generating substrate includes glycerol, propylene glycol, water, nicotine and, optionally, one or more flavorants. The aerosol-generating substrate may include nicotine.

The term "tobacco material" refers to a material or substance including tobacco, which includes tobacco blends or flavored tobacco, for example.

The term "cartomizer" refers to a combination of cartridge and atomizer that is part of an aerosol-generating system.

In at least one example embodiment, the cartridge of the aerosol-generating system includes a transparent region forming at least a portion of a sidewall and a light source fixed to the sidewall and configured to transmit light into a liquid containing volume.

The aerosol-generating system may include one or more of a housing, a power unit, an aerosolizer, a cartridge, and a mouthpiece. The aerosolizer may be operably coupled to the power unit to receive power. The aerosolizer may be operably coupled to the cartridge to aerosolize an aerosol-generating substrate contained in the cartridge. The mouthpiece may be coupled to the cartridge. The housing may be coupled to one or more other components, which may be at least partially contained by the housing.

The components of the aerosol-generation system may be coupled in various ways. In at least one example embodiment, the cartridge and the aerosolizer may be formed together as a single unit (for example, a cartomizer). In another example embodiment, the cartridge and the aerosolizer may be formed as separate units, and the aerosolizer may be coaxially positioned within the cartridge. In yet another example embodiment, the cartridge and the aerosolizer may be formed as separate units, and the aerosolizer and the cartridge may be sequentially positioned along a length of the aerosol-generating system.

The cartridge may include a housing defining a liquid volume, a transparent region, and a light source. The liquid volume may contain a liquid aerosol-generating substrate (such as an e-liquid). The liquid volume may be about 2 millilitres (ml) to about 6 ml.

The liquid aerosol-generating substrate may be an e-liquid. The e-liquid may be a mixture of one or more of: propylene glycol, glycerin, polyethylene, polyethylene glycol, and nicotine. The e-liquid may also include one or more other components, such as flavouring agents.

The housing of the cartridge may have any suitable shape capable of defining a liquid volume. The housing may have a generally cylindrical shape. The housing of the cartridge may include a sidewall that extends from a first end or mouthpiece end, to a second end or power supply end. The sidewall has an inner surface, and an outer surface separated by a thickness of the sidewall. The sidewall may define a cylindrical shape. The mouthpiece end of the housing may be tapered.

The housing of the cartridge may be formed of any suitable material or suitable materials. Non-limiting examples of the housing materials include at least one of a polymer, a glass, and a metal.

The inner surface of the cartridge housing may include a light reflecting layer. The light reflecting layer may cover a portion of or all the inner surface. The light reflecting layer may be coupled to the sidewall. The light reflecting layer may cover the entire inner surface except for the transparent region and the light entry region, if present. The light reflecting layer may cover at least about 50% of the inner surface area of the housing sidewall.

The light reflecting layer may be formed of any suitable material capable of reflecting light (that is visible light or light having a wavelength range from about 400 to about 800 nm). The light reflecting layer may reflect at least about 50% of incident light, or at least about 75% of incident light, or at least about 90% of incident light. Types of light reflecting layers include: a metallic layer or film, or a multi-layer optical reflective film. The metallic layer may include silver or aluminium material. The multi-layer optical reflective film may have at least 95% light reflection, such as in commercially available under the trade designation Enhanced Specular Reflector (or ESR) film from 3M Company (Minnesota, United States). Higher light reflection may provide greater the light efficiency.

The transparent region may provide a visual window into the cartridge, particularly into the liquid volume of the cartridge, so that the liquid level or liquid can be monitored. The transparent region may be transparent to visible light (for example, light having a wavelength range from about 400 to about 800 nanometres). The transparent region may be surrounded or bounded by non-transparent portions of the housing sidewall.

The transparent region may form a portion of the sidewall. The transparent region may form at least about 10% of the surface area of the housing sidewall. The transparent region may form the entire cartridge sidewall, or 100% of the surface area of the housing sidewall.

The transparent region may be a separate piece fixed to the sidewall of the cartridge. The transparent region may be a unitary piece formed integral with the sidewall.

Suitable material for the transparent region may include one or more of; a glass, a polymeric material, or a polycrystalline ceramic material. The material may include a transparent glass, or a transparent polymer, or a transparent polycrystalline material. Transparent polymeric material may include an acrylic material, a polycarbonate material, or a polyolefin material. The material may have suitable optical properties for providing the visual window into the cartridge. The transparent region may exhibit an optical clarity of at least about 75% or at least about 85%.

The transparent region may include an anti-reflective coating or layer. The anti-reflective layer may be disposed on the outer surface of the sidewall in the transparent region. The anti-reflective layer may prevent the reflection of incident light. Non-limiting examples of suitable material to form the anti-reflective layer include magnesium fluoride or fluoropolymers.

The light source may transmit light into the liquid volume. The light source forms a portion of the cartridge. The light source forms a portion of the housing sidewall. The light source may be fixed to the sidewall. For example, the light source may be fixed to the inner surface of the sidewall, may be fixed the outer surface of the sidewall, or may form a portion of the sidewall or housing. The light source may be spaced apart from the first end or second end of the housing. The light source may not be fixed to, or direct light into, the first end or second end of the housing.

When the light source is fixed to the sidewall outer surface, light may be transmitted through the housing or sidewall. The light source may be disposed in a recess in the housing or sidewall. For example, the light source may be disposed in a recess formed in the outer surface of the sidewall. The recess or sidewall may be light transparent to the light wavelengths emitted by the light source.

When the light source forms a portion of the housing, the light may be disposed in an annular ring. The annular ring may circumscribe the liquid volume. The annular ring may be co-axial with the adjacent portions of the housing or sidewall. The housing or sidewall may form a light guide that transmits light along the sidewall and into the liquid containing volume.

The light source may be optically coupled to the sidewall, or the light source may be optically coupled to liquid contained within the housing.

The light source may be any suitable type of light generator. The light source may emit visible light. The light source may include one or more of a solid-state light source or a radioluminescence material. The solid-state light source may include a light-emitting diode (LED).

In at least one example embodiment, a light source includes one LED or radioluminescence material positioned at one location. The location may be a middle point of the sidewall along a longitudinal direction. The middle point may not be closer to a power battery facing end portion than a mouthpiece facing end portion.

In at least one example embodiment, a light source includes LEDs or radioluminescence material positioned at several locations. The locations may be uniformly distributed on the sidewall inner surface.

In at least one example embodiment, a light source includes one sheet-shaped LED, such as an organic LED (OLED), or one sheet of radioluminescence material. The sheet-shaped light source may be positioned on the sidewall.

In at least one example embodiment, the radioluminescence material may include radium, promethium, or tritium.

In at least one example embodiment, the light source may provide light in wavelengths that may provide improved illumination of e-liquid compared to other wavelengths. The light source may emit light wavelengths from about 420 to about 720 nm.

A light transparent layer may cover the light source and the electrical interface. The light transparent layer may electrically insulate the light source while still allowing light to transmit through the layer. The light transparent layer may protect or encapsulate the light source while still allowing light to transmit through the layer.

The light source may be operably coupled to an electrical interface and may be electrically connected to the electrical interface. The electrical interface may be operably coupled to the power supply of the power unit when the device is assembled. In at least one example embodiment, the electrical interface may couple to the cartridge connector of the power unit. The electrical interface may be coupled to the sidewall or housing. The electrical interface may extend from the light source along the sidewall to the power supply end of the housing.

A light sensor may be operably coupled to the light source. The light source, in combination with the light sensor and optionally the controller, may be used to adjust illumination of the light source, and associated liquid contents within the housing or cartridge, in response to low light conditions. In at least one example embodiment, the light source may be activated in lower lighting to facilitate visibility into the cartridge. The light source may be dimmed, for example, when the lighting is almost completely dark to adjust for the natural dilation of the eyes of the user. The light source may be dimmed to adjust for bright ambient light and conserve power, for example.

A puff sensor may be operably coupled to the light source. The light source, in combination with the puff sensor and optionally the controller, may be used to adjust illumination of the light source, and associated liquid contents within the housing or cartridge, in response to inhalation by the user. In at least one example embodiment, the light source may be deactivated during inhalation since the user may not be about to view the transparent window, thus conserving energy. The light source may be activated once the puff sensor detects the end of an inhalation. The puff sensor may activate a different light source or different coloured light source during inhalation. In at least one example embodiment, during vaping a red light source may illuminate to indicate vapor formation and a different coloured light may illuminate at the end of the inhalation cycle.

When the system is assembled, the mouthpiece may be coupled to the cartridge at, proximate to, or adjacent to the mouthpiece end of the cartridge. The mouthpiece may facilitate exiting of aerosol from the system. The mouthpiece may engage with the mouthpiece end of the aerosolizer. Additionally, the mouthpiece may engage and seal to the cartridge. With such arrangement, when a puff is taken on the mouthpiece, air may enter from air inlet holes in the aerosolizer, mix in the aerosolizer with the aerosol from e-liquid, and travel to the mouthpiece.

The power unit may supply electric current to various components of the aerosol-generating system for operation. The power unit may include a power supply, an aerosolizer connector, a cartridge connector, and an actuation switch. One actuation switch may be utilized to activate both the aerosolizer and the light source. A first actuation switch may be utilized to power the aerosolizer and a second actuation switch may be utilized to power the light source.

The power supply may provide electrical power to one or more of the light source, the aerosolizer, and the control circuit. The power supply may be a battery. The power supply may be rechargeable.

The power supply may include an electrical interface that operably couples to the electrical interface of the cartridge to power the light source. In particular, the electrical interface of the power supply may be complementary to the electrical interface of the cartridge light source. The electrical interface of the power supply may be part of the cartridge connector.

The aerosolizer connector may be disposed on an aerosolizer engagement portion of the power unit. The cartridge connector may be disposed on a cartridge engagement portion of the power unit. The aerosolizer connector and the cartridge connector may be operably coupled to the aerosolizer and the cartridge, respectively, in an assembled state of the aerosol-generating system. In at least one example embodiment, the aerosolizer connector and the cartridge connector may be in electrical connection with the aerosolizer and the cartridge, respectively.

When the system is assembled, the cartridge may be in threaded engagement with the power unit. In at least one example embodiment, the power supply end of the cartridge may be in threaded engagement with the cartridge engagement portion of the power unit.

The actuation switch may control supply of electric current from the battery to each of the cartridge connector and the atomizer connector. The switch may be used to activate the aerosolizer and the cartridge light in response to engagement. The power unit may include only a single switch. In at least one example embodiment, the power unit may include two or more switches. In at least one example embodiment, engaging the switch may active only the cartridge light. A separate switch may be used to activate the aerosolizer.

The switch may utilize any suitable mechanism to receive input from the an adult vaper. In at least one example embodiment, the switch may include a button or lever. In response to being pressed, toggled, or otherwise manipulated, the switch may be activated or deactivated.

In at least one example embodiment, the switch, a puff sensor may control supply of electric current from the power supply to each of the cartridge connector and the aerosolizer connector. The puff sensor may be positioned within an airflow channel in the aerosol-generating system to detect when a user inhales, or puffs, on the mouthpiece. Non-limiting types of puff sensors may include one or more of a vibrating membrane, a piezoelectric sensor, a mesh-like membrane, a pressure sensor (for example, a capacitive pressure sensor), and an airflow switch.

The aerosolizer may be coupled to the aerosolizer engagement portion of the power unit. The aerosolizer may be operably coupled to the power supply using the aerosolizer connector.

When the system is assembled, the aerosolizer may be disposed within the cartridge at, proximate to, or adjacent to the power supply end of the cartridge. In at least one example embodiment, the aerosolizer may be coupled to the power supply end of the cartridge.

The aerosolizer may be compatible with a liquid aerosol-generating substrate. The aerosolizer may include a heater, a heater coil, a chemical heat source (such as a carbon heat source), or any suitable means that heats the substrate to generate aerosol. A heating element of the aerosolizer may be disposed adjacent to the substrate housing and heated to produce aerosol from the liquid substrate.

Part of the aerosolizer may also be coupled to the cartridge of the housing. In at least one example embodiment, a heater coil may include a susceptor coupled to the cartridge and an inductive coil coupled to the power unit configured to transfer energy to the susceptor for heating the substrate.

The aerosolizer may include an atomizer, which may not rely on heat to generate aerosol. The atomizer may mechanically generate aerosol from the liquid substrate.

In at least one example embodiment, the aerosolizer includes a heating unit that extracts a portion of e-liquid from the cartridge and vaporizes the e-liquid. The aerosol of vaporized e-liquid may then exit pass through and exit the device. When the system is assembled, the aerosolizer may be in fitted arrangement with the aerosolizer engagement portion of the power unit, such that the aerosolizer is in electrical communication with the aerosolizer connector of the power unit. With such assembly, the aerosolizer may be coaxially positioned within the cartridge, such that a liquid storage area is defined between the aerosolizer and the cartridge. Upon actuation by the switch, or puff sensor, the aerosolizer may extract a small amount of e-liquid from the cartridge and then vaporize the e-liquid.

The control circuit may be operably coupled to one or more of the light source, the switch, the aerosolizer, and an optional light sensor to facilitate functionality of the aerosol-generating system. In at least one example embodiment, the control circuit may include a controller electrically connected to one or more components. The controller, including any processors and memory, may be sized and shaped to fit into housings of aerosol-generating systems.

One or more of the controllers described herein may include a processor, such as a central processing unit (CPU), computer, logic array, or other device capable of directing data coming into or out of the aerosol-generating device. The controller may include one or more computing devices having memory, processing, and communication hardware. The controller may include circuitry used to couple various components of the controller together or with other components operably coupled to the controller. The functions of the controller may be performed by hardware and/or as computer instructions on a non-transient computer readable storage medium.

The processor of the controller may include any one or more of a microprocessor, a microcontroller, a digital signal processor (DSP), an application specific integrated circuit (ASIC), a field-programmable gate array (FPGA), and/or equivalent discrete or integrated logic circuitry. In some examples, the processor may include multiple components, such as any combination of one or more microprocessors, one or more controllers, one or more DSPs, one or more ASICs, and/or one or more FPGAs, as well as other discrete or integrated logic circuitry. The functions attributed to the controller or processor herein may be embodied as software, firmware, hardware, or any combination thereof. While described herein as a processor-based system, an alternative controller may utilize other components such as relays and timers to achieve the desired results, either alone or in combination with a microprocessor-based system.

In at least one example embodiment, the system, method, and/or interface may be implemented using one or more computer programs using a computing apparatus, which may include one or more processors and/or memory. Program code and/or logic described herein may be applied to input data/information to perform functionality described herein and generate desired output data/information. The output data/information may be applied as an input to one or more other devices and/or methods as described herein or as would be applied in a known fashion. In view of the above, it will be readily apparent that the controller functionality as described herein may be implemented in any manner known to one skilled in the art.

The controller may, in combination with the switch or the puff sensor, illuminate the cartridge during or after a puff. The controller may be able to illuminate the light source independent of activating the aerosolizer.

In at least one example embodiment, the light source is illuminated when a puff is not detected. The light source may be illuminated a different colour, or change colour, when a puff is detected.

In at least one example embodiment, different coloured light sources may be illuminated based on air flow rate or air flow pressure.

In at least one example embodiment, a visual artistic effect mode may be activated when a puff is detected, particularly when the light source is configured to display an image or motion image. The light source may be used for visual artistic effects during puffing because, in general, the liquid level may not be checked while puffing, but rather may be checked before and/or after puffing.

The controller may, in combination with the liquid level indicator, illuminate the light source based on the liquid level. Additionally, or alternatively, other light sources having different colors or different locations within the cartridge may be illuminated based on the liquid level.

FIG. 1 shows an aerosol-generating system 10 including a power unit 12, a cartridge 14, an aerosolizer 16, and a mouthpiece 18. Various arrangements of the aerosol-generating system 10 may be contemplated.

In at least one example embodiment, the cartridge 14 and the atomizer 16 of the aerosol-generating system 10 may be formed together as a single unit, termed cartomizer. In at least one example embodiment (shown in FIG. 1), the cartridge 14 and the atomizer 16 may be formed as separate units, with the atomizer 16 coaxially positioned within the cartridge 14. In at least one example embodiment, the cartridge 14 and the atomizer 16 may be formed as separate units, with the atomizer 16 and the cartridge 14 being sequentially positioned along a length of the aerosol-generating system 10.

In at least one example embodiment, the cartridge 14 and the atomizer 16 are formed as separate units, while the atomizer 16 is coaxially positioned within the cartridge 14 (see FIG. 1). Application of at least one example embodiment may be applicable to other example embodiments of the aerosol-generating system 10.

In at least one example embodiment, the power unit 12 supplies electric current to various other components of the aerosol-generating system 10, for operation. The power unit 12 includes a battery (not shown), an atomizer connector 20, a cartridge connector 22, and an actuation switch 24. The atomizer connector 20 is disposed on an atomizer engagement portion 26 of the power unit 12. The cartridge connector 22 is disposed on a cartridge engagement portion 28 of the power unit 12. The atomizer connector 20 and the cartridge connector 22 are in electrical connection to the atomizer 16 and the cartridge 14 respectively, in an assembled state of the aerosol-generating system 10. The actuation switch 24 controls a supply of electric current from the battery (not shown) to each of the cartridge connector 22 and the atomizer connector 20.

The cartridge 14 may include a hollow tank or reservoir that stores and carries an e-liquid. The e-liquid is typically a mixture of one or more of propylene glycol, glycerin, polyethylene, polyethylene glycol, and nicotine. Inclusion of one or more other components, such as flavouring agents, in the e-liquid may also be contemplated. The cartridge 14 includes a battery facing end portion 30 and a mouthpiece facing end portion 32. In assembly, the battery facing end portion 30 of the cartridge 14 is in threaded engagement with the cartridge engagement portion 28 of the power unit 12, such that the cartridge 14 is in threaded engagement with the power unit 12. Structure and arrangement of the cartridge 14 will be described later in details.

The atomizer 16 is a heating unit that extracts a portion of e-liquid from the cartridge 14 and vaporizes it. In assembly, the atomizer 16 is in fitted arrangement with the atomizer engagement portion 26 of the power unit 12, such that the atomizer 16 is in electrical communication with the atomizer connector 20 of the power unit 12. With such assembly, the atomizer 16 is coaxially positioned within the cartridge 14, such that a liquid storage area (not shown) is defined between the atomizer 16 and the cartridge 14. Upon actuation, the atomizer 16 extracts a small amount of e-liquid from the cartridge 14 and then atomizes (vaporizes) it.

The mouthpiece 18 facilitates exit of the aerosol from the device. The mouthpiece 18 engages with a vapor outlet end 34 of the atomizer 16. Additionally, the mouthpiece 18 sealably engages with the cartridge 14. When a puff is taken, air enters from the air inlet holes (not shown) in the atomizer 16, mixes with the aerosolized (vaporized) e-liquid in the atomizer 16, and travels to the mouthpiece 18.

Figure 2:
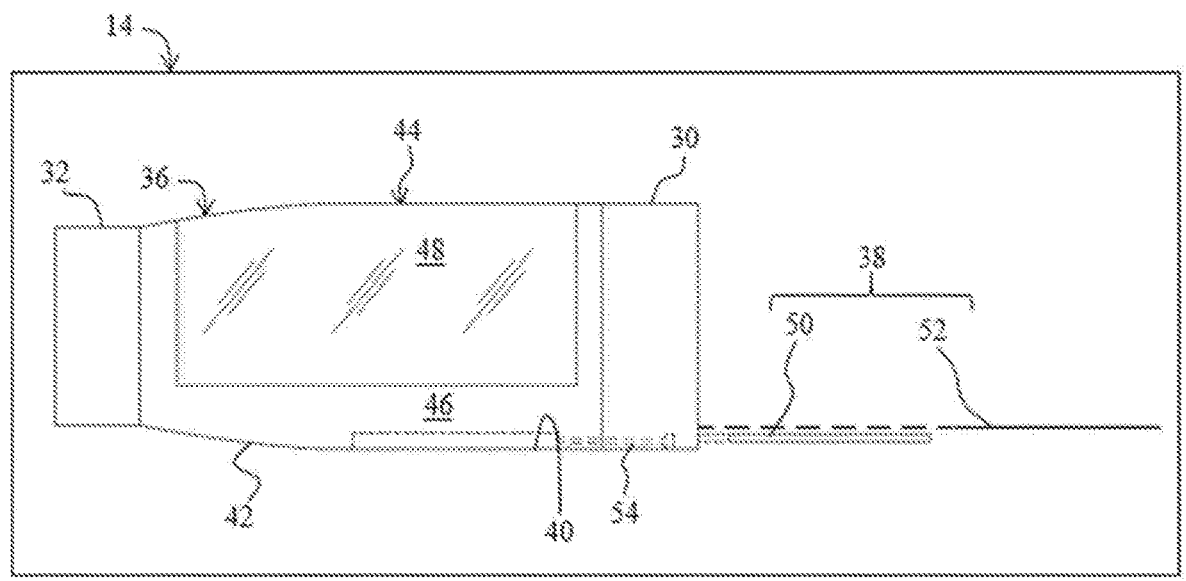
FIG. 2 is a schematic illustration of a cartridge with a light source fixed to an inner surface of the housing sidewall according to at least one example embodiment.
Figure 3:
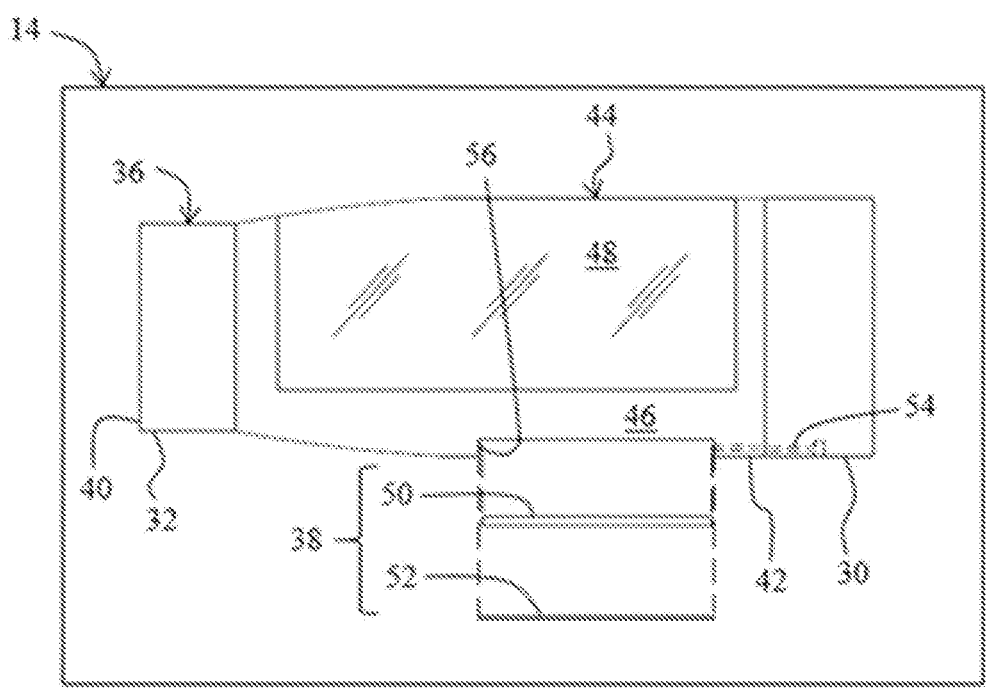
FIG. 3 is a schematic illustration of a cartridge with a light source fixed to an outer surface of the housing sidewall according to at least one example embodiment.
Figure 4:
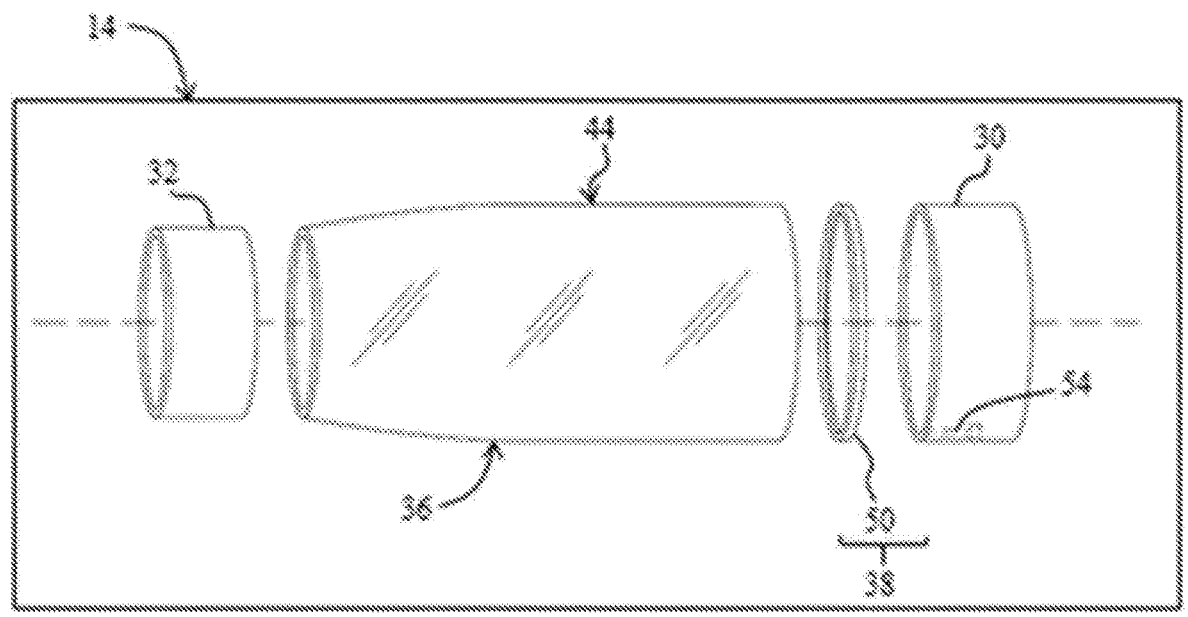
FIG. 4 is a schematic illustration of a cartridge with a light source forming an annular portion of the housing sidewall according to at least one example embodiment.

In at least one example embodiment, as is shown in FIG. 2, FIG. 3, and FIG. 4, the cartridge 14 includes a housing 36 and a lighting arrangement 38. Various arrangements of the housing 36 and the lighting arrangement 38 may be contemplated, as described below.

In at least one example embodiment, the lighting arrangement 38 may be positioned on an inner surface 40 of the housing 36 of the cartridge 14, as illustrated in FIG. 2.

In at least one example embodiment, the lighting arrangement 38 may be positioned on an outer surface 42 of the housing 36 of the cartridge 14, as illustrated in FIG. 3.

In at least one example embodiment, the lighting arrangement 38 may be positioned within the housing 36 of the cartridge 14, as illustrated in FIG. 4.

In at least one example embodiment, as shown in FIG. 2, when the lighting arrangement 38 is positioned on the inner surface 40 of the housing 36, the housing 36 includes the battery facing end portion 30, the mouthpiece facing end portion 32, and an intermediate or sidewall portion 44. The intermediate or sidewall portion 44 may include a base peripheral frame 46 and a transparent peripheral window 48. The transparent peripheral window 48, described herein, may define the transparent region of the sidewall 44.

The base peripheral frame 46 is formed such that the base peripheral frame 46 focuses the light emitted by the lighting arrangement 38 towards the transparent peripheral window 48. In at least one example embodiment, at least a portion of the inner surface 40 of the base peripheral frame 46 is coated with a layer of focusing or light reflecting material to focus the light emitted by the lighting arrangement 38 towards the transparent peripheral window 48. The layer of focusing or light reflecting material may include, such as but not limited to, a sheet of aluminum reflector, a transparent sheet with a silver polished back surface, multilayer light reflecting film and the like.

The transparent peripheral window 48 is fixedly attached to the base peripheral frame 46. The transparent peripheral window 48 is made of a transparent material, such as but not limited to, a plate glass, an acrylic sheet, and a polycrystalline ceramic sheet. The transparent peripheral window 48 is formed, such that the transparent peripheral window 48 reduces and/or prevents reflection of external light. In at least one example embodiment, the outer surface 42 of the transparent peripheral window 48 is coated with an anti-reflective layer, which reduces and/or prevents reflection of external light from the transparent peripheral window 48. A material of the anti-reflective layer is selected based on the material of the transparent peripheral window 48. In at least one example embodiment, the intermediate portion 44 including the transparent peripheral window 48 made of crown glass, may include the layer of anti-reflective material made of magnesium fluoride or fluoropolymers, to prevent reflection of external light from the transparent peripheral window 48.

In at least one example embodiment, the transparent peripheral window 48 may be fixedly attached to the base peripheral frame 46. Also, the transparent peripheral window 48 and the base peripheral frame 46 may be formed as a singular integrated component.

In at least one example embodiment, when the lighting arrangement 38 is positioned on the inner surface 40 of the housing 36, the lighting arrangement 38 includes a light source 50 and a cover 52.

In at least one example embodiment, the light source 50 is a strip of a number of LED's (light emitting diodes). The light source 50 is positioned on the inner surface 40 of the base peripheral frame 46. The light source 50 is configured to emit a light, to illuminate the housing 36 of the cartridge 14. In at least one example embodiment, the light source 50 emits the light of a specific wavelength of about 420 to about 720 nm, to better illuminate the housing 36 of the cartridge 14. The wavelength of the light emitted by the light source 50 is dependent on a refractive index of each of the e-liquid, the recess 56, and the transparent peripheral window 48 of the housing 36 of the cartridge 14.

The cover 52 is attached to the inner surface 40 of the base peripheral frame 46, such that the light source 50 is positioned between the inner surface 40 and the cover 52. The cover 52 is a transparent cover that protects the light source 50.

In at least one example embodiment, the cartridge 14 also includes an internal electrical wiring 54 that connects the light source 50 to the cartridge connector 22 of the power unit 12, when the cartridge 14 is assembled with the power unit 12.

FIG. 2 illustrates an exploded view of the cartridge 14 illustrating the lighting arrangement 38 positioned on the inner surface 40 of the housing 36 according to at least one example embodiment.

In at least one example embodiment, as shown in FIG. 3, when the lighting arrangement 38 is positioned on the outer surface 42 of the housing 36, the housing 36 includes the battery facing end portion 30, the mouthpiece facing end portion 32, and the intermediate or sidewall portion 44. The intermediate or sidewall portion 44 includes the base peripheral frame 46 and the transparent peripheral window 48.

The base peripheral frame 46 includes a recess 56. Further, the base peripheral frame 46 is formed such that the base peripheral frame 46 focuses the light emitted by the lighting arrangement 38 towards the transparent peripheral window 48. In at least one example embodiment, at least a portion of the inner surface 40 of the base peripheral frame 46, adjacent the recess 56, is coated with a layer of focusing or light reflecting material to focus the light emitted by the lighting arrangement 38 towards the transparent peripheral window 48. The layer of focusing or light reflecting material, is described above.

The transparent peripheral window 48 is fixedly attached to the base peripheral frame 46. The transparent peripheral window 48 is made of a transparent material, as described above. The transparent peripheral window 48 is formed, such that the transparent peripheral window 48 reduces and/or prevents reflection of external light. In at least one example embodiment, the outer surface 42 of the transparent peripheral window 48 is coated with an anti-reflective layer, which reduces and/or prevents reflection of external light from the transparent peripheral window 48. A material of the anti-reflective layer is selected based on the material of the transparent peripheral window 48, as described above.

In at least one example embodiment, the transparent peripheral window 48 may be fixedly attached to the base peripheral frame 46. Also, the transparent peripheral window 48 and the base peripheral frame 46 may be a singular integrated component.

In at least one example embodiment, when the lighting arrangement 38 is positioned on the outer surface 42 of the housing 36, the lighting arrangement 38 includes a light source 50 and a cover 52. In at least one example embodiment, the light source 50 is a strip of a number of LED's (light emitting diodes). The light source 50 is positioned within the recess 56 of the base peripheral frame 46. The light source 50 is configured to emit a light, to illuminate the housing 36 of the cartridge 14. In at least one example embodiment, the light source 50 emits the light of a specific wavelength of about 420 to about 720 nm, to better illuminate the housing 36 of the cartridge 14. The wavelength of the light emitted by the light source 50 is dependent on a refractive index of each of the e-liquid, the recess 56, and the transparent peripheral window 48 of the housing 36 of the cartridge 14.

The cover 52 is attached to the recess 56 of the base peripheral frame 46, such that the light source 50 is positioned between the recess 56 and the cover 52. The recess 56 uniformly distributes a light degenerated by the light source 50 within the interior of the housing 36, upon actuation of the light source 50. Further, the cartridge 14 may also include the internal electrical wiring 54 that connects the light source 50 to the power unit 12, when the cartridge 14 is assembled with the power unit 12.

FIG. 3 describes an exploded view of the cartridge 14 illustrating the lighting arrangement 38 positioned external to the housing 36 according to at least one example embodiment.

FIG. 4 illustrates when the lighting arrangement 38 is positioned within the housing 36 of the cartridge 14, or when the lighting arrangement 38 forms a portion of the housing 36 or sidewall 44 according to at least one example embodiment. Here the housing 36 may be substantially tubular or a cylindrical structure that includes the battery facing end portion 30, the mouthpiece facing end portion 32, and an intermediate or sidewall portion 44. The lighting arrangement 38 forms an annular element that is coaxial with the cylindrical or tubular sidewall 44. The intermediate or sidewall portion 44 may be entirely made of a transparent material, such as but not limited to, a plate glass, an acrylic sheet, and a polycrystalline ceramic sheet. The intermediate or sidewall portion 44 may be formed, such that the intermediate or sidewall portion 44 reduces and/or prevents reflection of external light. In at least one example embodiment, the outer surface 42 of the intermediate or sidewall portion 44 is coated with an anti-reflective layer, which prevents reflection of external light incident on the intermediate or sidewall portion 44. A material of the anti-reflective layer is selected based on the material of the intermediate or sidewall portion 44. In at least one example embodiment, the intermediate portion 44 made of crown glass, may include the layer of anti-reflective material made of magnesium fluoride or fluoropolymers.

In at least one example embodiment, when the lighting arrangement 38 is positioned within the housing 36 of the cartridge 14, or when the lighting arrangement 38 forms a portion of the housing 36 or sidewall 44, the lighting arrangement 38 includes a light source 50. The light source 50 is an annular strip of a number of LED's (light emitting diode). The light source 50 is positioned between the battery facing end portion 30 and along the intermediate or sidewall portion 44 of the housing 36. The light source 50 illuminates a body of the intermediate or sidewall portion 44 of the housing 36, upon actuation. In at least one example embodiment, the cartridge 14 also includes an internal electrical wiring 54 that connects the light source 50 to the power unit 12, when the cartridge 14 is assembled with the power unit 12.

FIG. 4 describes an exploded view of the cartridge 14 illustrating the lighting arrangement 38 positioned within the housing 36 of the cartridge 14, or when the lighting arrangement 38 forms a portion of the housing 36 or sidewall 44 according to at least one example embodiment.

In at least one example embodiment of the cartridge 14 of the aerosol-generating system 10, actuation of the light source 50 may be in response to vaping. In at least one example embodiment, the light source 50 may be selectively actuated with use of the actuation switch 24 of the power unit 12. As the actuation switch 24 is pressed for operation of the aerosol-generating system 10, the light unit 50 illuminates an interior of the cartridge 14 of the aerosol-generating system 10. In at least one example embodiment, the light source 50 may be selectively actuated with use of a separate actuation switch. As the actuation switch 24 is pressed, the light source 50 illuminates an interior of the cartridge 14 of the aerosol-generating system 10. In at least one example embodiment, the light source 50 may be automatically actuated with use of a control unit (optionally a processor of the aerosol-generating system 10) of the power unit 12. During low environment lighting conditions, the control unit may automatically actuate the light source 50 of the lighting arrangement 38.

Example embodiments described above illustrations. However, other example embodiments may be made without departing from the scope as defined in the claims, and it is to be understood that the example embodiments described above are not intended to be limiting.

As used herein, the singular forms "a," "an," and "the" encompass embodiments having plural referents, unless the content clearly dictates otherwise.

As used herein, "or" is generally employed in its sense including "and/or" unless the content clearly dictates otherwise. The term "and/or" means one or all the listed elements or a combination of any two or more of the listed elements.

As used herein, "have," "having," "include," "including," "comprise," "comprising" or the like are used in their open-ended sense, and generally mean "including, but not limited to". It will be understood that "consisting essentially of," "consisting of," and the like are subsumed in "comprising," and the like.

We claim:

1. A cartridge for use with an aerosol-generating system, the cartridge comprising:

a housing defining a liquid containing volume, the housing including,
   a sidewall extending from a first end to a second end,
   a mouthpiece facing end portion coupled to the first end of the sidewall,
   a light source defining an annular ring forming an exterior portion of the housing and configured to transmit light into the liquid containing volume, the light source coupled to the second end of the sidewall, and
   a battery facing end portion coupled to the light source; and
a transparent region forming at least a portion of the sidewall.

2. The cartridge according to claim 1, further comprising: an electrical interface electrically connected to the light source and coupled to the sidewall, the housing, or both the sidewall and the housing.

3. The cartridge according to claim 1, wherein a portion of an inner surface of the sidewall includes a light reflective layer.

4. The cartridge according to claim 1, wherein the transparent region comprises an anti-reflective coating.

5. The cartridge according to claim 1, wherein the light source comprises a solid-state light source.

6. The cartridge according to claim 5, wherein the solid-state light source is a light emitting diode.

7. The cartridge according to claim 1, wherein the light source comprises a radioluminescence material.

8. The cartridge according to claim 7, wherein the radioluminescence material comprises radium, promethium, tritium, or any combination thereof.

9. The cartridge according to claim 1, wherein the light source emits light wavelengths in a range from 420 to 720 nm.

10. An aerosol-generating system comprising,
a power supply;
an atomizer electrically coupled to the power supply; and
a cartridge including,
   a housing defining a liquid containing volume, the housing including,
   a sidewall extending from a first end to a second end,
   a mouthpiece facing end portion coupled to the first end of the sidewall,
   a light source defining an annular ring forming an exterior portion of the housing and configured to transmit light into the liquid containing volume, the light source coupled to the second end of the sidewall, and
   a battery facing end portion coupled to the light source; and
a transparent region forming at least a portion of the sidewall.

11. The aerosol-generating system according to claim 10, wherein the power supply comprises a complementary electrical interface electrically coupled to an electrical interface of the light source.

12. The aerosol-generating system according to claim 10, further comprising:
   a control circuit coupled to the light source configured to illuminate the light source independently from activating the atomizer.

13. The aerosol-generating system according to claim 10, further comprising:
   a light sensor coupled to the light source.

14. The cartridge according to claim 1, wherein the annular ring is coaxial with the second end of the sidewall and the battery facing end portion.

* * * * *